US009109202B2

(12) United States Patent
Spanholtz

(10) Patent No.: US 9,109,202 B2
(45) Date of Patent: Aug. 18, 2015

(54) METHODS AND MEANS FOR STEM CELL PROLIFERATION AND SUBSEQUENT GENERATION AND EXPANSION OF PROGENITOR CELLS, AS WELL AS PRODUCTION OF EFFECTOR CELLS AS CLINICAL THERAPEUTICS

(75) Inventor: Jan Spanholtz, Duesseldorf (DE)

(73) Assignee: IPD-THERAPEUTICS B.V., BH Bilthoven (NL)

( * ) Notice: Subject to any disclaimer, the term of this patent is extended or adjusted under 35 U.S.C. 154(b) by 1975 days.

(21) Appl. No.: 12/088,471

(22) PCT Filed: Sep. 28, 2006

(86) PCT No.: PCT/NL2006/000484
§ 371 (c)(1),
(2), (4) Date: Jul. 16, 2008

(87) PCT Pub. No.: WO2007/037682
PCT Pub. Date: Apr. 5, 2007

(65) Prior Publication Data
US 2009/0017539 A1    Jan. 15, 2009

(30) Foreign Application Priority Data

Sep. 28, 2005 (EP) .................................. 05077221

(51) Int. Cl.
*C12N 5/074* (2010.01)
*C12N 5/0783* (2010.01)
*C12N 5/0789* (2010.01)
*C12N 5/071* (2010.01)

(52) U.S. Cl.
CPC ............ *C12N 5/0607* (2013.01); *C12N 5/0646* (2013.01); *C12N 5/0647* (2013.01); *C12N 5/0692* (2013.01); *C12N 2501/105* (2013.01); *C12N 2501/115* (2013.01); *C12N 2501/125* (2013.01); *C12N 2501/145* (2013.01); *C12N 2501/165* (2013.01); *C12N 2501/21* (2013.01); *C12N 2501/22* (2013.01); *C12N 2501/235* (2013.01); *C12N 2501/2306* (2013.01); *C12N 2501/26* (2013.01); *C12N 2501/91* (2013.01); *C12N 2506/03* (2013.01)

(58) Field of Classification Search
None
See application file for complete search history.

(56) References Cited

U.S. PATENT DOCUMENTS

| | | | | |
|---|---|---|---|---|
| 5,199,942 A | * | 4/1993 | Gillis | 604/4.01 |
| 5,206,223 A | * | 4/1993 | Vlodavsky et al. | 514/56 |
| 6,316,257 B1 | * | 11/2001 | Flyer et al. | 435/372.3 |
| 2003/0082806 A1 | * | 5/2003 | Berenson et al. | 435/372 |

OTHER PUBLICATIONS

"O-acetyl-L-carnitine hydrochloride." Available online at <http://www.sigmaaldrich.com/catalog/ProductDetail.do?D7=0&N5=SEARCH_CONCAT_PNO%7CBRAND_KEY&N4=A6706%7CSIGMA&N25=0&QS=ON&F=SPEC>. Accessed on Jan. 9, 2012. 1 page.*

Yu, Haixin et al: "Flt3 ligand promotes the generation of a distinct CD34+ human natural killer cell progenitor that responds to interleukin-15", Blood, W.B. Saunders, Philadelphia, VA, US, vol. 92, No. 10, Nov. 15, 1998, pp. 3647-3657, XP002318933, ISSN: 0006-4971, entire document.

Carayol, Geraldine et al: "NK cells differentiated from bone marrow, cord blood and peripheral blood stem cells exhibit similar phenotype and functions", European Journal of Immunology, vol. 28, No. 6, Jun. 1998, pp. 1991-2002, XP002406970, ISSN: 0014-2980, entire document.

Muench, Marcus O. et al.: "Differential effects of interleukin-3, interleukin-7, interleukin 15, and granulocyte-macrophage colony-stimulating factor in the generation of natural killer and B cells from primitive human fetal liver progenitors", Experimental Hematology (Charlottesville), vol. 28, No. 8, Aug. 2000, pp. 961-973, XP002406971, ISSN: 0301-472X, entire document.

Mrozek, E. et al.: "Role of interleukin-15 in the development of human CD56+ natural killer cells from CD34+ hematopoietic pregenitor cells", Blood, W.B. Saunders, Philadelphia, VA, US, vol. 87 No. 7, 1996, pp. 2632-2640, XP002318934, ISSN: 0006-4971, entire document.

Gehling, U.M. et al.: "In vitro differentiation of endothelial cells from AC133-positive progenitor cells", Blood, W.B. Saunders Company, Orlando, FL, US, vol. 95, No. 10, May 15, 2000, pp. 3106-3112, XP002254113, ISSN: 0006-4971, the whole document.

Pillich, R.T. et al.: "Reduction of apoptosis through the mitochondrial pathway by the administration of acetyl-1-carnitine to mouse fibroblasts in culture", Experimental Cell Research, San Diego, CA, US, vol. 306, No. 1, May 15, 2005, pp. 1-8, XP004876357, ISSN: 0014-4827, the whole document.

Okamoto, Toru et al.: "Effect of heparin addition on expansion of cord blood hematopoietic progenitor cells in three-dimensional coculture with stromal cells in nonwoven fabrics.", Journal of Artificial Organs: The Official Journal of the Japanese Society for Artificial Organs. 2004, vol. 7, No. 4, 2004, pp. 194-202, XP002406974, ISSN: 1434-7229, the whole document.

* cited by examiner

*Primary Examiner* — Lora E Barnhart Driscoll
(74) *Attorney, Agent, or Firm* — Hoffmann & Baron, LLP

(57) ABSTRACT

The invention provides means and methods for stem cell proliferation and subsequent generation and expansion of progenitor cells. The invention in particular provides media and other culture conditions for the same. The cells are preferably used as effector cells as clinical therapeutics.

55 Claims, No Drawings

METHODS AND MEANS FOR STEM CELL PROLIFERATION AND SUBSEQUENT GENERATION AND EXPANSION OF PROGENITOR CELLS, AS WELL AS PRODUCTION OF EFFECTOR CELLS AS CLINICAL THERAPEUTICS

This application is the U.S. National Phase of, and Applicant claims priority from, International Application Number PCT/NL2006/000484 filed 28 Sep. 2006 and European Application bearing Serial No. 05077221.9 filed 28 Sep. 2005, which are incorporated herein by reference.

BACKGROUND OF THE INVENTION

The invention relates to the field of modern medical biology. In particular the invention relates to stem cell technology. More in particular the invention relates to perinatal stem cell technology, in particular umbilical cord stem cell technology.

Stem cells are primal undifferentiated cells which have the ability for self-renewal and the ability to differentiate into other cell types. This ability allows them to act as a repair system for the body, replenishing other cells as long as the organism is alive.

Stem cells are categorized by potency which describes the specificity of that cell.

Totipotent stem cells are cells that have the ability of self renewal and are capable of differentiating into any and all cell type to form an entire new organism. They are typically produced from the fusion of an egg and sperm cell. Cells produced by the first few divisions of the fertilized egg cell are also totipotent. These cells can grow into any cell type without exception.

Pluripotent stem cells are the descendants of totipotent cells and can grow into any cell type except for totipotent stem cells.

Multipotent stem cells can produce only cells of a closely related family of cells (e.g. hematopoietic stem cells can differentiate into blood cells such as red blood cells, white blood cells and platelets).

Progenitor (sometimes called unipotent) cells can produce only one cell type; but, have the property of self-renewal which distinguishes them from non-stem cells.

Stem cells are also categorized according to their source, as either adult or embryonic.

Adult stem cells are undifferentiated cells found among differentiated cells of a specific tissue and are mostly multipotent cells. They are more accurately called somatic stem cells, because they need not come from adults but can also come from children or umbilical cords.

Embryonic stem cells are cells obtained from the undifferentiated inner mass cells of a blastocyst, an early stage embryo that is 50 to 150 cells.

Blood from the the placenta and umbilical cord that are left over after birth is one source of adult stem cells. It is collected by removing the umbilical cord, cleansing it and withdrawing blood from the umbilical vein.

Red blood cells can be removed from the cord blood and the remaining cells can be used or stored (e.g. in liquid nitrogen).

Stem cells themselves are useful in many applications of so-called regenerative medicine. They have been used to treat heart disease, repair spinal chords and many other diseases where tissues of all kinds needed to be replaced.

Stem cells can also be used to produce certain kinds of differentiated cells that are effector cells in certain diseases.

Unfortunately however, stem cells are present in the body of a mammal in minute quantities only. Often they are present in organs or tissues that can not easily be reached. Embryonic stem cell are also not easily obtainable and only in minute quantities. Moreover, there are some ethical concerns in growing embryos merely for the purpose of producing stem cells. There is a need therefore for methods for multiplying available stem cells and/or primitive lineage specific progeny thereof, without differentiating into less potent descendants. Totipotent stem cells should remain totipotent after expansion and not turn into pluripotent stem cells, pluripotent stem cells should remain pluripotent, etc. In some instances the change into a less potent descendant may be acceptable (at least to a certain extent) as long as the potential for self renewal and at least multipotency is retained.

SUMMARY OF THE INVENTION

Although stem cells have the ability of self-renewal, maintaining stem cells in culture, is not an easy task. In its broadest sense the present invention provides a medium and a method for stem cell culture and/or expansion and/or differentiation comprising a number of elements that are extremely suitable for just that purpose.

Thus in one embodiment the invention provides a medium for culturing, expanding and/or differentiating stem cells, said medium comprising a basic cell culture medium, 1-20% human serum, 2-10 mmol/l O-acetyl-L-carnitine or a functional equivalent thereof, 40-80 mg/l N-desulphated-N-acetylated heparin or a functional equivalent thereof and a combination of suitable cytokines, preferably encompassing three or more of thrombopoietin, flt-3 ligand, stem cell factor, G-CSF, GM-CSF, IL-6, MIP-I-α, and LIF, and further conventional supplements, such as L-glutamine, antibiotics, ascorbic acid, selenium selenite and ethanolamine. The cytokines given are chosen for their functions. For some of the cytokines given there are other cytokines which will at least in part be able to perform the same function. Those can then of course substitute the listed ones.

Preferably a medium according to the invention comprises about 3-8, more preferably about 5 mmol/l of O-acetyl-L-carnitine. A functional equivalent may be present in different amounts which are equivalent in activity to the amounts given for O-acetyl-L-carnitine.

Preferably a medium according to the invention comprises about 50-70, more preferably about 60 mg/l of N-desulphated-N-acetylated heparin. A functional equivalent may be present in different amounts which are equivalent in activity to the amounts given for N-desulphated-N-acetylated heparin.

The amounts of cytokine added are conventional in the art, preferred amounts are given in the examples, but 10% deviations in amount are very well acceptabler and within the scope of the present invention.

Many basic media are known. A selection is given below, but many more may be bought from companies such as invitrogen. Basic media include but are not limited to BEM (Basic Eagle Medium), DMEM (Dulbecco's modified Eagle Medium), Glasgow minimal essential medium, M199 basal medium, HAM F10, HAM F12, Iscove's DMEM, Leibovitz L15, MCDB, McCoy 5A, etc.

Combinations of these basic media can also be used and combinations of DMEM and HAM F12 are preferred for some differentiation media according to the invention. The amounts given herein are typically suitable for cultures which are started with about 1 million cells per ml. The amounts may be adapted for different amounts of cells with which cultures are started.

The media according to the invention can be varied in their serum content, preferably together with a different combination of cytokines to provide either an expansion medium or a differentiation medium.

Thus, in one embodiment of the present invention a medium and a method for proliferating stem cells with subsequent generation of primitive lineage specified progenitor cells, particularly stem cells from cord blood, is provided in a form that stem cell proliferation produces one daughter stem cell and one primitive progenitor stem cell, the latter with the ability of extensive self-renewal and functional maturation. Typically from 1 million cells of a stem cell enriched population $1\times10^8$ primitive progenitors can be generated while maintaining the stem cell pool. Each primitive progenitor is capable to produce $>1\times10^3$ functional maturated effector cells. The stem cell enriched population may be isolated CD34+ cells and/or CD133+cells. The addition of monocyte enriched CD14+ cells enhances the amplification as well as maturation of the desired cells.

The present invention in said embodiment provides a medium for expanding stem cells comprising a basic cell culture medium, 10-20% human serum, 2-10 mmol/l O-acetyl-L-carnitine or a functional equivalent thereof, 40-80 mg/l N-desulphated-N-acetylated heparin or a functional equivalent thereof and a combination of suitable cytokines, preferably encompassing three or more of thrombopoietin, flt-3 ligand, stem cell factor, G-CSF, GM-CSF, IL-6, MIP-I-α, and LIF, and further conventional supplements, such as L-glutamine, antibiotics, ascorbic acid, selenium selenite and ethanolamine.

Preferably, a medium for expansion according to the invention comprises about 15% of human serum, preferably AB serum. Preferably a medium for expansion according to the invention comprises about 5 mmol/l O-acetyl-L-carnitine. Preferably a medium for expansion according to the invention comprises 60 mg/l N-desulphated-N-acetylated heparin. The preferred basic medium is RPMI1640.

In a further preferred embodiment a medium for expansion according to the invention comprises thrombopoietin, flt-3 ligand, stem cell factor, G-CSF, GM-CSF, IL-6, MIP-I-α, LIF, VEGF, bFGF, IL-3 and IL-7 in conventional amounts, preferably in the amounts given in the examples.

In another embodiment the invention provides differentiation media for differentiation into Natural Killer cell progenitors, preferably two media for two steps in differentiation, for which media the amount of human serum lies between 5-10%. Preferably the amount of serum is around 8%. Preferably a medium for differentiation according to the invention comprises about 5 mmol/l O-acetyl-L-carnitine. Preferably a medium for differentiation according to the invention comprises 60 mg/l N-desulphated-N-acetylated heparin. The preferred basic medium is a mixture of 2:1 (v/v) DMEM and HAM-F12.

A preferred combination of cytokines for the first step in differentiation is TPO, FLT-3L, SCF, IL-7, VEGF, IL-2, GM-CSF, G-CSF, LIF, MIP-I-α and IL-6. This medium is preferably applied after expansion of stem cells for about three days, preferably expansion in an expansion medium according to the invention.

Preferably this first differentiation step into natural killer cell progenitors is followed by a further differentiation step about three days later (at 6 days since harvest or thawing) with yet a different secondary differentiation medium according to the invention in which the cells should be cultured for about 9-24, preferably 12-22 days).

A second differentiation medium according to the invention comprises 5-10% human serum (preferably AB), preferably about 8% human serum.

Preferably a second medium for differentiation according to the invention comprises about 5 mmol/l O-acetyl-L-carnitine. Preferably a second medium for differentiation according to the invention comprises 60 mg/l N-desulphated-N-acetylated heparin. The preferred basic medium is a mixture of 2:1 (v/v) DMEM and HAM-F12. A preferred combination of cytokines for the second step in differentiation is TPO, FLT-3, SCF, IL-7, IL-15, IL-2, GM-CSF, G-CSF, LIF, IL-6, MIP-I-α.

This medium should be refreshed between 3-8, preferably around 6 days.

The invention also encompasses methods for maintaining while proliferating stem cells with the generation and expansion of progenitor cells, in particular stem cells from umbilical cord blood, comprising harvesting stem cells from cord blood, culturing said cells in a medium according to the invention and separating the expanded cells from said medium. The invention further comprises methods for differentiating stem cells into NK progenitor cells comprising culturing said stem cells, in particular stem cells derived from umbilical cord blood, in a differentiation medium according to the invention and preferably culturing said stem cells in a first and a second differentiation medium in a scheme as given in the detailed description below. Culturing must occur under conventional suitable conditions typically encompassing temperatures of around 37 degrees Celsius, 100%RH, 10%O2 and 5-7%CO2.

The invention also encompasses proliferated and maintained stem cells produced by a process according to the invention.

The invention also encompasses natural killer progenitor cells produced by a method according to the invention.

In a further embodiment the invention comprises a set of media (kit of parts) for proliferation and maintenance of stem cells, in particular derived from cord blood) and generation of primitive NK progenitor cells, comprising an expansion medium according to the invention, a first and a second deifferentiation medium according to the invention and preferably an instruction leaflet for use of the media.

The NK progenitor cells can be differentiated into mature and functional NK cells recognizing a desired target by specific receptors on their surface known to the expert in the field (CD56, CD16, CD107, NKG2a/CD94, NKp-antigens, KIR-receptors). These mature and functional NK cells can be generated in vitro by extending the culture period 2-3 more weeks. However, as cellular therapeutic the injection of the primitive progenitors and maturation in vivo is preferred. These NK cells can be used in the treatment of any kind of human disease preferably all malignant diseases such as tumors, cancer, in particular leukemias, ovarian, colon and skin cancers, Breast, Brain and Lung cancers, Cervical cancer and metastases of all kinds of cancer, particularly to the liver, as well as all viral diseases, in particular HIV, HCV, and other chronic viral diseases Methods for (expanding and) differentiating stem cells into NK progenitor cells and onward into NK cells are also part of the present invention.

The target specific NK cells produced by these methods are also part of the present invention. Pharmaceutical compositions comprising progenitor cells or mature NK cells produced according to the invention and further comprising usual constituents of such compositions are also part of the present invention. Doses for such pharmaceutical compositions are generally expressed in the number of viable cells present in such a composition. Said number should be between $1-9\times10^6$ NK-IC or $>1-10\times10^8$ mature NK-cells per kg body weight of a subject to be treated.

In another embodiment the invention comprises a medium for differentiating (expanded) stem cells into Vascular progenitor cells.

In this embodiment a preferred (first) differentiation medium comprises a basic medium (preferably M199 basal medium) with about 7-12, preferably about 10% human serum preferably AB), about 4-6, preferably about 5 mmol/l of O-acetyl-L-carnitine, about 60 mg/l N-desulphated-N-acetylated heparin.

The following combination of cytokines is preferred: SCGF, VEGF, Angiopoietin-1, angiopoietin-2, bFGF, IGF, TPO, FLT-3L, Il-1β, GM-CSF, G-CSF, LIF, MIP-I-α and 11-6. The amounts again are preferably those given in the examples, although 10% deviations will typically be acceptable. Other usual constituents for culture media as given herein before may of course be added.

It is preferred to further enhance the differentiation into VP cells by culturing the cells in a second differentiation medium. The scheme preferred is given in the detailed description, although such a scheme is not critical. The lengths of the different culture steps can be varied.

This second culture medium mainly differs from the first in the amount of human serum present, which should be about 1-4%, preferably around 2%.

The preferred set of cytokines is SCGF, VEGF, bFGF, IGF, TPO, FLT-3L and IL-1β.

The invention also encompasses vascular progenitor cells produced by a method according to the invention. These cells can be used for treatment of any cardiovascular disease involving the generation of newe blood vessels or new endothelium. Pharmaceutical compositions comprising vascular progenitor cells are also part of the present invention. The amount of cells per dose will typically comprise at least $1\times10^6$ viable cells per dose.

In a further embodiment the invention comprises a set of media (kit of parts) for expansion and differentiation of stem cells, in particular derived from cord blood) into vascular progenitor cells, comprising an expansion medium according to the invention, a first and a second differentiation medium according to the invention and preferably an instruction leaflet for use of the media.

Methods for differentiating stem cells into vascular progenitor cells and onward into functional new endothelium and blood vessels leading to revascularisation of the tissue are also part of the present invention.

The invention will be explained in more detail in the following detailed description.

DETAILED DESCRIPTION

The following description discloses a method of in vitro generation of cellular therapeutics for clinical use that can be derived from small aliquots of postembryonic stem cells. This procedure is characterized by culturing postembryonic stem cells in a specifically formulated medium with a defined composition as well as a defined culture handling procedure to yield sufficient progenitors for clinical application.

The invention disclosed in here is at least in part based on the technical problem that for the treatment of malignant diseases, i.e. cancer, leukaemias and lymphomas as well as for cardiovascular diseases the availability of cellular therapies is very limited. With the exception of very few haematopoietic stem cell transplantations using umbilical cord blood (UCB), postembryonic stem cells have not been used for targeted cellular treatment in a non-allogeneic transplant setting without high dose chemotherapy/radiation-conditioning of the patient mainly due to the fact, that sufficient directed progenitor cells for cellular therapy are not available yet. In addition, these cells are alloreactive and cause severe graft-versus host disease in the recipient if treatment and cellular product are not optimal chosen.

The technical problem was at least partly solved in this invention by providing practicable procedures to generate sufficient numbers of progenitors for selected treatments as indicated herein before. The technical problem of selected progenitor generation of human postembryonic stem cells for clinical application could be solved by applying both well defined procedures of in vitro culture steps as well as specific changes of the culture conditions as described in the method section. These procedures allow for the first time the production of vascular progenitors (VP-cells) and/or Natural-Killer-cell (NK-cell)-progenitors for clinical application from small postembryonic stem cell aliquots.

The following postembryonic stem cells that can be obtained beginning from week 12 after gestation from foetal liver, perinatal umbilical cord blood (UCB), human bone marrow or G-CSF stimulated peripheral blood can be isolated and used for cultivation procedures according to the invention. The person skilled in the art knows methods for the collection of these stem cells, whereby the harvest from perinatal umbilical cord or placental blood is preferred for the procedures according to the invention.

In a further preferred embodiment of the procedures according to the invention a functional proof of the final cellular therapeutic is performed consecutive to cultivation. Especially preferred is the proof of progenitor features of Natural Killer Cells (NK-cells) as well as vascular progenitor cells (VP-cells) by established in vitro assay systems.

The Following Example Illustrates the Invention:
1. Initiation of the in vitro Culture:

Small aliquots of postembryonic stem cells (minimum 25 ml of human umbilical cord blood; an amount that is well below the required minimum amount for clinical banking) are processed according standard operating procedures of red cell lysis to obtain nucleated cells for further processing. As a option cells can be further purified by immunomagnetic cell separation according to the manufacturer (Miltenyi-Biotec, Germany) into enriched CD34+ cells (or alternatively CD133+ cells) and additionally CD14+ cells can be separated as well. The person of skill in this field will be able to perform these cell separations according to the manufacturer. These cells are put in culture flasks or Teflon bags that contain the so called <u>G</u>lycostem-<u>T</u>echnology-<u>I</u>nitiation or GTI-medium: The medium in this example consists of RPMI1640 (Invitrogen Inc.) containing 15% human AB-serum (Cambrex Inc.), O-acetyl-L-carnitine (OALC, Sigma Chemicals) or derivatives in a final concentration of 5 mmol/l, N-desulfated-N-acetylated heparin (Seigagaku Amerika Inc.) in a concentration of 60 mg/l. The following recombinant human cytokines (if not specifically mentioned all cytokines have been provided by Stem Cell Technology Inc. or R&D Systems): thrombopoietin (TPO; 25 ng/ml); flt-3 Ligand (FLT-3L; 25 ng/ml), stem cell factor (SCF; 25 ng/ml), interleukin-7 (IL-7; 25 ng/ml), vascular endothelial growth factor (VEGF; 10 ng/ml), interleukin-3 (IL-3; 2,5 ng/ml), basic fibroblast growth factor (bFGF; 10 ng/ml), insulin like growth factor (IGF; 10 ng/ml), granulocyte-macrophage-colony-stimulating factor (GM-CSF; 10 pg/ml Immunex Corp., Seattle, Wash.), granulocyte-colony-stimulating factor (G-CSF, 250 pg/ml; Amgen, Thousand Oaks, Calif.), Leukemia-inhibitory factor (LIF; 50 pg/ml), Macrophage-inflammatory protein-1alpha (200 pg/ml; MIP-I alpha) and interleukin-6 (IL-6; 50 pg/ml). Additional supplements are L-glutamine (2 mmol/l; Invitrogen), penicillin (1000 U/ml), streptomycin 100 U/ml (Invitrogen), 25 µM 2-mercaptoethanol-beta (Invitrogen) ascorbic acid (20 mg/ml, Sigma), selenium selenite (50 µmol, Sigma), ethanolamine (50 µmol Sigma). The final ratio of medium to inoculated cells is $1 \times 10^6$ total cells per 1 ml of medium. The initiation of culture can be performed in 2 alternative ways:

a) inoculation of nucleated cells after red cell lysis in GTI-medium
b) inoculation of separated CD34+ cells (or alternatively CD133+ cells) together with separated CD14+ cells as supplement in GTI-medium at a ratio of 1 cell CD34+ [or alternatively CD133+ cells] : 1cell CD14+)
c) inoculation of separated CD34+ cells (or alternatively CD133+ cells) in GTI-medium Cells are cultivated in the aforementioned medium and ratios under appropriate conditions. Appropriate conditions exemplary with regard to adequate culture containers, temperature, relative humidity, $O_2$ and $CO_2$ content of the gas phase are known to the expert. Preferentially the cells are cultivated in the aforementioned medium under the following conditions: (a) 37° C., (b) 100% relative humidity, (c) 10% $O_2$ and (d) 5% to 7% $CO_2$.

2. Differentiation Decision at Day 3 in vitro:

At day 3 of culture the first medium supplementation is performed. At this point the cellular suspension culture is driven into either NK-cell differentiation or vascular progenitor (VP)-differentiation.

This can be done in 2 ways:
a) The entire product is further differentiated in only one of the two differentiation pathways (either NK- or VPC-differentiation)
b) The product is divided as required and one aliquot is further differentiated into NK-progenitors, the other one into VPC-progenitors.
c) Adherent cells are differentiated into VPC, non-adherent cells are further differentiated into NK-progenitors.

2.1. Generation of Natural Killer Cell Progenitor Product

The designated amount of the initial cell culture product are supplemented at day 3 after initiation of culture with Glycostem-Technology-Nk-day3 (GTNKd3)-medium (1 ml GTNKd3-medium per $1 \times 10^6$ total input cells). At day 6 the suspension culture is supplemented with Glycostem-Technology-Nk-day6 (GTNKd6)-medium (2 ml GTNKd6-medium per $1 \times 10^6$ total input cells). From day 9 after initiation of culture the medium supplementation occurs the following way:

Day 9: addition of 4 ml GTNKd6-medium per $1 \times 10^6$ total input cells

Day 12: addition of 8 ml GTNKd6-medium per $1 \times 10^6$ total input cells

Day 15: addition of 16 ml GTNKd6-medium per $1 \times 10^6$ total input cells

At day 18-21 all cells are harvested and 2 washing steps in PBS containing 1% human AB-serum are performed according to standard operating procedures known to the person skilled in the field. Afterwards cells are resuspended in physiological NaCl-solution (0,9%) for infusion into the patient. After infusion, the NK-IC-progenitors, specifically generated to maturate within the patients body (in vivo) and finally differentiate in vivo into functional Natural Killer cells, that are able to kill specific tumor cell targets. For this reason the patient is preferably treated immediately after infusion with subcutaneous IL-2 (Proleukin©) at a dose of $2 \times 10^6$ IU/kg body weight.

A small aliquot (200 cells total) is used for quality assurance control of the product to enumerate the number of NK-cell progenitors in the final product using the well established NK-IC assay as described in the literature (Miller et al., 1999; Punzel et al., 1999).

Experimental example: In 3 independent UCB-samples (amount between 26-59 ml; TNC [total nucleated cells] ranging from $2\text{-}6 \times 10^8$) NK-IC progenitors could be generated with a total cell count between $1,1\text{-}1,9 \times 10^8$. Since 1 single NK-IC generates >1000 mature NK-cells in vivo, a minimum of 10 packages each with the capacity to generate $1 \times 10^8$/kg body weight mature NK-cells can be cryopreserved until use according to standard operating procedures known to the expert in the field.

Media:

GTNKd 3-medium

The medium consists of DMEM/Ham's 12-Medium (Invitrogen Inc.) volume-ratio 2:1 (V/V) with 8% human AB-serum (Cambrex Inc.), O-acetyl-L-carnitine (OALC, Sigma Chemicals) or derivatives in a final concentration of 5 mmol/l, N-desulfated-N-acetylated heparin (Seigagaku Amerika Inc.) in a concentration of 60 mg/l. The following recombinant human cytokines (if not specifically mentioned all cytokines have been provided by Stem Cell Technology Inc. or R&D Systems): thrombopoietin (TPO; 25 ng/ml); flt-3 Ligand (FLT-3L; 25 ng/ml), stem cell factor (SCF; 25 ng/ml), interleukin-7 (IL-7; 25 ng/ml), vascular endothelial growth factor (VEGF; 10 ng/ml), interleukin-2 (Proleukin© [Chiron]; 750 U/ml), granulocyte-macrophage-colony-stimulating factor (GM-CSF; 10 pg/ml Immunex Corp., Seattle, Wash.), granulocyte-colony-stimulating factor (G-CSF, 250 pg/ml; Amgen, Thousand Oaks, Calif.), Leukemia-inhibitory factor (LIF; 50 pg/ml), Macrophage-inflammatory protein-1alpha (200 pg/ml; MIP-I alpha) and interleukin-6 (IL-6; 50 pg/ml). Additional supplements are L-glutamine (2 mmol/l; Invitrogen), penicillin (1000 U/ml), streptomycin 100 U/ml (Invitrogen), 25 µM 2-mercaptoethanol-beta (Invitrogen) ascorbic acid (20 mg/ml, Sigma), selenium selenite (50 µmol, Sigma), ethanolamine (50 µmol Sigma).

GTNKd 6-medium

The medium consists of DMEM/Ham's 12-Medium (Invitrogen Inc.) volume-ratio 2:1 (V/V) with 8% human AB-serum (Cambrex Inc.), O-acetyl-L-carnitine (OALC, Sigma Chemicals) or derivatives in a final concentration of 5 mmol/l, N-desulfated-N-acetylated heparin (Seigagaku Amerika Inc.) in a concentration of 60 mg/l. The following recombinant human cytokines (if not specifically mentioned all cytokines have been provided by Stem Cell Technology Inc. or R&D Systems): thrombopoietin (TPO; 25 ng/ml); flt-3 Ligand (FLT-3L; 25 ng/ml), stem cell factor (SCF; 25 ng/ml), interleukin-7 (IL-7; 25 ng/ml), interleukin-15 (IL-15; 25 ng/ml), interleukin-2 (Proleukin© [Chiron]; 1500 U/ml), granulocyte-macrophage-colony-stimulating factor (GM-CSF; 10 pg/ml Immunex Corp., Seattle, Wash.), granulocyte-colony-stimulating factor (G-CSF, 250 pg/ml; Amgen, Thousand Oaks, Calif.), Leukaemia-inhibitory factor (LIF; 50 pg/ml), Macrophage-inflammatory protein-1alpha (200 pg/ml; MIP-I alpha) and interleukin-6 (IL-6; 50 pg/ml). Additional supplements are L-glutamine (2 mmol/l; Invitrogen), penicillin (1000 U/ml), streptomycin 100 U/ml (Invitrogen), 25 µM 2-mercaptoethanol-beta (Invitrogen) ascorbic acid (20 mg/ml, Sigma), selenium selenite (50 µmol, Sigma), ethanolamine (50 µmol Sigma).

NK-IC-assay for quality control: This assay enumerates the number of primitive NK-cell-progenitors that have been generated at day 18 of culture. Each single NK-IC progenitor can give rise to >1000 mature and functional NK-cells. Thus, this assay provides a valuable readout and quality control instrument for the product. The small aliquot of expanded cells (200 cells) will be plated into 96 well plates in limiting dilution assays in AFT024-cocultures supplemented with medium that consist of DMEM/Ham's 12-Medium 2:1 (V/V) with 20% human heat-inactivated AB-Serum and 20 mg/ml ascorbic acid, 50 μmol selenium selenite, 25 μmol β-mercaptoethanol, 50 μmol ethanolamine, 1000 U/ml IL-2, 5 ng/ml IL-3 [only initially], 10 ng/ml Flt-3L, 10 ng/ml SCF und 20 ng/ml IL-7. After 5-7 weeks of culture cells were analysed phenotypically for mature and functional NK-cells (CD56+/CD3−/CD16/NKp30/NKp44/NKp46,NKG2A/CD94, CD107).

2.2. Generation of Vascular Progenitor Cell Products

The designated amount of the initial cell culture product has to be placed on fibronectin coated tissue culture treated 175 cm² flasks at day 3 after initiation and needs to be supplemented further with Glycostem-Technology-Vascular-Progenitor day 3-medium (GTVPd3)-medium (15 ml GTVPd3-medium per 175 cm² flasks). At day 6 all non-adherent cells have to be removed and medium supplementation has to occur from day 6 the following way:

Day 6: exchange of 15 ml GTVPd6-medium per flask
Day 12: exchange of 15 ml GTVPd6-medium per flask
Day 18: exchange of 15 ml GTVPd6-medium per flask
Day 24: exchange of 15 ml GTVPd6-medium per flask At day 18-28 all cells are harvested using cell dissociation solution (Becton-Dickinson) and 2 washing steps in PBS containing 1% human AB-serum are performed according to standard operating procedures known to the expert in the field. Afterwards cells are resuspended in physiological NaCl-solution (0,9%) for infusion into the patient A small aliquot (1000 cells total) is used for quality assurance control of the product to enumerate the number of VP-cell progenitors in the final product using well established Vascular Progenitor cell detection methods that are well known to the person of skill in the field. Phenotypic verification of endothelial progenitor cells has to include CD31, vWF, and DiL-uptake as it is well known to the skilled person in the field. Several publications for the detection of VP-cells have been published in the literature (Gehling et al., 2000; Loges et al., 2004).

Experimental example: In 1 UCB-samples (amount 39 ml; TNC $2,2 \times 10^8$; CD34+$0,9 \times 10^6$) VP-cell-colonies as defined are generated with a total cell count after harvest between $1,1-1,9 \times 10^6$. cells. These cells are cryopreserved until use according to standard operating procedures known to the expert in the field.

Media:
GTVPd3-medium

The medium consists of M199 basal medium supplemented with 10% human AB-serum (Cambrex Inc.), O-acetyl-L-carnitine (OALC, Sigma Chemicals) or derivatives in a final concentration of 5 mmol/l, The following recombinant human cytokines (if not specifically mentioned all cytokines have been provided by Stem Cell Technology Inc. or R&D Systems): Stem cell growth factor (50 ng, SCGF) vascular endothelial growth factor (VEGF; 50 ng/ml), angiopoietin-1 (10 ng, R&D-systems), angiopoietin-2 (10 ng, R&D-systems), basic fibroblast growth factor (bFGF; 10 ng/ml), insulin like growth factor (IGF; 10 ng/ml), thrombopoietin (TPO; 25 ng/ml); flt-3 Ligand (FLT-3L; 25 ng/ml), interleukin-1α (IL-1, 20 ng/ml), granulocyte-macrophage-colony-stimulating factor (GM-CSF; 10 pg/ml Immunex Corp., Seattle, Wash.), granulocyte-colony-stimulating factor (G-CSF, 250 pg/ml; Amgen, Thousand Oaks, Calif.), Leukemia-inhibitory factor (LIF; 50 pg/ml), Macrophage-inflammatory protein-1alpha (200 pg/ml; MIP-I alpha) and interleukin-6 (IL-6; 50 pg/ml). Additional supplements are L-glutamine (2 mmol/l; Invitrogen), penicillin (1000 U/ml), streptomycin (100 U/ml, Invitrogen), 25 μM 2-mercaptoethanol-beta (Invitrogen) ascorbic acid (20 mg/ml, Sigma).

GTVPd 6-medium

The medium consists of M199 basal medium supplemented with 2% human AB-serum (Cambrex Inc.), O-acetyl-L-carnitine (OALC, Sigma Chemicals) or derivatives in a final concentration of 5 mmol/l, The following recombinant human cytokines (if not specifically mentioned all cytokines have been provided by Stem Cell Technology Inc. or R&D Systems): Stem cell growth factor (50 ng, SCGF) vascular endothelial growth factor (VEGF; 50 ng/ml), basic fibroblast growth factor (bFGF; 10 ng/ml), insulin like growth factor (IGF; 10 ng/ml), thrombopoietin (TPO; 25 ng/ml); flt-3 Ligand (FLT-3L; 25 ng/ml), interleukin-1β (IL-1, 20 ng/ml). Additional supplements are L-glutamine (2 mmol/l; Invitrogen), penicillin (1000 U/ml), streptomycin (100 U/ml, Invitrogen), 25 μM 2-mercaptoethanol-beta (Invitrogen) ascorbic acid (20 mg/ml, Sigma).

REFERENCES

Gehling, U. M., Ergun, S., Schumacher, U., Wagener, C., Pantel, K., Otte, M., Schuch, G., Schafhausen, P., Mende, T., Kilic, N., et al. (2000). In vitro differentiation of endothelial cells from AC133-positive progenitor cells. Blood 95, 3106-3112.

Loges, S., Fehse, B., Brockmann, M. A., Lamszus, K., Butzal, M., Guckenbiehl, M., Schuch, G., Ergun, S., Fischer, U., Zander, A. R., et al. (2004). Identification of the adult human hemangioblast. Stem Cells Dev 13, 229-242.

Miller, J. S., McCullar, V., Punzel, M., Lemischka, I. R., and Moore, K. A. (1999). Single adult human CD34(+)/Lin-/CD38(−) progenitors give rise to natural killer cells, B-lineage cells, dendritic cells, and myeloid cells. Blood 93, 96-106.

Punzel, M., Wissink, S. D., Miller, J. S., Moore, K. A., Lemischka, I. R., and Verfaillie, C. M. (1999). The myeloid-lymphoid initiating cell (ML-IC) assay assesses the fate of multipotent human progenitors in vitro. Blood 93, 3750-3756.

The invention claimed is:

1. A medium for culturing, expanding and/or differentiating stem cells, said medium comprising a basic cell culture medium, 1-20% human serum in relation to the volume of culture medium, 2-10 mmol/l O-acetyl-L-carnitine in relation to the volume of culture medium, 40-80 mg/l N-desulphated-N-acetylated heparin N-desulphated-N-acetylated heparin in relation to the volume of culture medium and a combination of cytokines.

2. A medium according to claim 1, which medium comprises about 3-8 mmol/l of O-acetyl-L-carnitine in relation to the volume of culture medium.

3. A medium according to claim 1, which comprises about 50-70 mg/l of N-desulphated-N-acetylated heparin in relation to the volume of culture medium.

4. A medium according to claim 1 for expanding stem cells, comprising a basic cell culture medium, 10-20% human serum in relation to the volume of culture medium, 2-10 mmol/l O-acetyl-L-carnitine in relation to the volume of culture medium, 40-80 mg/l N-desulphated-N-acetylated heparin in relation to the volume of culture medium and a combination of cytokines.

5. A medium for expansion according to claim 4, comprising about 15% of human serum.

6. A medium for expansion according to claim 4, comprising about 5 mmol/l O-acetyl-L-carnitine in relation to the volume of culture medium.

7. A medium for expansion according to claim 4, comprising 60 mg/l N-desulphated-N-acetylated heparin in relation to the volume of culture medium.

8. A medium according to claim 4 wherein the basic medium is RPMI1640.

9. A medium for expansion according to claim 4, which comprises thrombopoietin (TPO), flt-3 ligand, stem cell factor, G-CSF, GM-CSF, IL-6, MIP-I-α, LIF, VEGF, bFGF, IL-3 and IL-7.

10. A medium according to claim 1 for differentiating stem cells into natural killer (NK) cell progenitors, comprising between 5-10% of human serum in relation to the volume of culture medium.

11. A medium according to claim 10 in which the amount of serum is around 8% in relation to the volume of culture medium.

12. A medium for differentiation according to claim 10, which comprises about 5 mmol/l O-acetyl-L-carnitine in relation to the volume of culture medium.

13. A medium for differentiation according to claim 10, which comprises 60 mg/l N-desulphated-N-acetylated heparin in relation to the volume of culture medium.

14. A medium according to claim 10, wherein the basic medium is a mixture of 2:1 (v/v) DMEM and HAM-F12.

15. An initial differentiation medium according to claim 10, wherein the combination of cytokines is TPO, FLT-3L, SCF, IL-7, VEGF, IL-2, GM-CSF, G-CSF, LIF MIP-Iα and IL-6.

16. A secondary differentiation medium according to claim 10, wherein the combination of cytokines is TPO, FLT-3 ligand, SCF, IL-7, IL-15, IL-2, GM-CSF, G-CSF, LIF, IL-6, and MIP-I-α.

17. A kit of parts for expanding and differentiating stem cells into NK progenitor cells, comprising an expansion medium comprising a basic cell culture medium, 10-20% human serum in relation to the volume of culture medium, 2-10 mmol/l O-acetyl-L-carnitine in relation to the volume of culture medium, 40-80 mg/l N-desulphated-N-acetylated heparin in relation to the volume of culture medium, and a combination of cytokines; and a differentiation medium comprising a basic cell culture medium, 5-10% human serum in relation to the volume of culture medium, 2-10 mmol/l O-acetyl-L-carnitine in relation to the volume of culture medium, 40-80 mg/l N-desulphated-N-acetylated heparin in relation to the volume of culture medium, and a combination of cytokines.

18. A kit of parts for expanding and differentiating stem cells into NK progenitor cells, comprising an expansion medium comprising a basic cell culture medium, 10-20% human serum in relation to the volume of culture medium, 2-10 mmol/l O-acetyl-L-carnitine in relation to the volume of culture medium, 40-80 mg/l N-desulphated-N-acetylated heparin in relation to the volume of culture medium, and a combination of cytokines; and an initial differentiation medium comprising a basic cell culture medium, 5-10% human serum in relation to the volume of culture medium, 2-10 mmol/l O-acetyl-L-carnitine in relation to the volume of culture medium, 40-80 mg/l N-desulphated-N-acetylated heparin in relation to the volume of culture medium, and a combination of cytokines comprising TPO, FLT-3L, SCF, IL-7, VEGF, IL-2, GM-CSF, G-CSF, LIF, MIP-I-α and IL-6.

19. A method for expanding and differentiating stem cells into NK progenitor cells, comprising expanding stem cells in a medium comprising a basic cell culture medium, 10-20% human serum in relation to the volume of culture medium, 2-10 mmol/l O-acetyl-L-carnitine in relation to the volume of culture medium, 40-80 mg/l N-desulphated-N-acetylated heparin in relation to the volume of culture medium and a combination of cytokines; and differentiating the expanded cells in a differentiation medium comprising a basic cell culture medium, 5-10% human serum in relation to the volume of culture medium, 2-10 mmol/l O-acetyl-L-carnitine in relation to the volume of culture medium, 40-80 mg/l N-desulphated-N-acetylated heparin in relation to the volume of culture medium, and a combination of cytokines.

20. A method for expanding and differentiating stem cells into NK progenitor cells, comprising expanding stem cells in a medium comprising a basic cell culture medium, 10-20% human serum in relation to the volume of culture medium, 2-10 mmol/l O-acetyl-L-carnitine in relation to the volume of culture medium, 40-80 mg/l N-desulphated-N-acetylated heparin in relation to the volume of culture medium and a combination of cytokines; and differentiating the expanded cells in an initial differentiation medium comprising a basic cell culture medium, 5-10% human serum in relation to the volume of culture medium, 2-10 mmol/l O-acetyl-L-carnitine in relation to the volume of culture medium, 40-80 mg/l N-desulphated-N-acetylated heparin in relation to the volume of culture medium, and a combination of cytokines comprising TPO, FLT-3L, SCF, IL-7, VEGF, IL-2, GM-CSF, G-CSF, LIF, MIP-I-α and IL-6.

21. A method for expanding stem cells comprising culturing said stem cells in a medium according to claim 4.

22. A method for differentiating stem cells comprising culturing stem cells into NK progenitor cells in a differentiation medium according to claim 10.

23. A method for differentiating stem cells comprising culturing stem cells into NK progenitor cells in an initial differentiation medium according to claim 15.

24. A medium according to claim 1, for differentiating stem cells into vascular progenitor cells, said medium comprising about 10% human serum in relation to the volume of culture medium.

25. A differentiation medium according to claim 24, wherein the basic medium is M199 basal medium.

26. An initial differentiation medium according to claim 24, wherein the combination of cytokines is SCGF, VEGF, Angiopoietin-1, angiopoietin-2, bFGF, IGF, TPO, FLT-3L, IL-1β, GM-CSF, G-CSF, LIF, MIP-I-α and 11-6.

27. A secondary differentiation medium according to claim 1, wherein the combination of cytokines comprises SCGF, VEGF, bFGF, IGF, TPO, FLT-3L and IL-IB and the amount of human serum is 1-4% in relation to the volume of culture medium.

28. A method for expanding and differentiating stem cells into vascular progenitor cells, comprising expanding stem cells in a medium for expanding stem cells comprising a basic cell culture medium, 10% human serum in relation to the volume of culture medium, 2-10 mmol/l O-acetyl-L-carnitine in relation to the volume of the culture medium, 40-80 mg/l N-desulphated-N-acetylated heparin in relation to the volume of the culture medium and a combination of cytokines, differentiating the expanded cells in a differentiation medium according to claim 24.

29. A method for expanding and differentiating stem cells into vascular progenitor cells, comprising expanding stem cells in a medium for expanding stem cells comprising a basic cell, culture medium, 10-20% human serum in relation to the volume of culture medium, 2-10 mmol/l O-acetyl-L-carnitine in relation to the volume of the culture medium, 40-80 mg/l N-desulphated-N-acetylated heparin in relation to the volume of the culture medium and a combination of cytokines, differentiating the expanded cells in an initial differentiation medium according to claim 26.

30. A method for differentiating stem cells comprising culturing stem cells, into vascular progenitor cells in a differentiation medium according to claim 24.

31. A method for differentiating stem cells comprising culturing stem cells, into vascular progenitor cells in an initial differentiation medium according to claim 26.

32. A kit of parts for expanding and differentiating stem cells into vascular progenitor cells, comprising an expansion medium for expanding stem cells comprising a basic cell culture medium, 10-20% human serum in relation to the volume of culture medium, 2-10 mmol/l O-acetyl-L-carnitine in relation, to the volume of culture medium, 40-80 mg/l N-desulphated-N-acetylated heparin in relation to the volume of the culture medium and a combination of cytokines, and a differentiation medium according to claim 24.

33. A kit of parts for expanding and differentiating stem cells into vascular progenitor cells, comprising an expansion medium for expanding stem cells comprising a basic cell culture medium, 10-20% human serum in relation to the volume of culture medium, 2-10 mmol/l O-acetyl-L-carnitine in relation to the volume of the culture medium, 40-80 mg/l N-desulphated-N-acetylated heparin in relation to the volume of the culture medium and a combination of cytokines, an initial differentiation medium according to claim 26.

34. A kit of parts according to claim 18 and a secondary differentiation medium for differentiating stem cells into Natural Killer cell progenitors comprising a basic cell culture medium, 1-20% human serum in relation to the volume of culture medium, 2-10 mmol/l O-acetyl-L-carnitine in relation to the volume of culture medium, 40-80 mg/l N-desulphated-N-acetylated heparin in relation to the volume of culture medium, and a combination of cytokines, wherein the combination of cytokines is TPO, FLT-3 ligand, SCF, IL-7, IL-15, IL-2, GM-CSF, G-CSF, LIF, IL-6, and MIP-I-α.

35. A method according to claim 20 and further differentiating the resulting cells in a secondary differentiation medium comprising thrombopoietin, flt-3 ligand, stem cell factor, G-CSF, GM-CSF, IL-6, MIP-I-α, LIF, VEGF, bFGF, IL-3 and IL-7 wherein the combination of cytokines is TPO, FLT-3 ligand, SCF, IL-7, IL-15, IL-2, GM-CSF, G-CSF, LIF, IL-6, and MIP-I-α.

36. A method according to claim 23 and further differentiating the resulting cells in a secondary differentiation medium comprising thrombopoietin, flt-3 ligand, stem cell factor, G-CSF, GM-CSF, IL-6, MIP-I-α, LIF, VEGF, bFGF, IL-3 and IL-7 wherein the combination of cytokines is TPO, FLT-3 ligand, SCF, IL-7, IL-15, IL-2, GM-CSF, G-CSF, LIF, IL-6, and MIP-I-α.

37. A method according to claim 29 and further differentiating the resulting cells in a secondary differentiation medium comprising thrombopoietin, flt-3 ligand, stem cell factor, G-CSF, GM-CSF, IL-6, MIP-I-α, LIF, VEGF, bFGF, IL-3 and IL-7 wherein the combination of cytokines is TPO, FLT-3, SCF, IL-7, IL-15, IL-2, GM-CSF, G-CSF, LIF, IL-6, and MIP-I-α.

38. A method according to claim 31 and further differentiating the resulting cells in a secondary differentiation medium comprising thrombopoietin, flt-3 ligand, stem cell factor, G-CSF, GM-CSF, IL-6, MIP-I-α, LIF, VEGF, bFGF, IL-3 and IL-7 wherein the combination of cytokines is TPO, FLT-3, SCF, IL-7, IL-15, IL-2, GM-CSF, G-CSF, LIF, IL-6, and MIP-I-α.

39. A kit of parts according to claim 33 and further differentiating the resulting cells in a secondary differentiation medium comprising thrombopoietin, flt-3 ligand, stem cell factor, G-CSF, GM-CSF, IL-6, MIP-I-α, LIF, VEGF, bFGF, IL-3 and IL-7 wherein the combination of cytokines is TPO, FLT-3, SCF, IL-7, IL-15, IL-2, GM-CSF, G-CSF, LIF, LIF, IL-6, and MIP-I-α.

40. A medium according to claim 1, wherein said cytokines encompass three or more of thrombopoietin, flt-3 ligand, stem cell factor, G-CSF, GM-CSF, IL-6, MIP-I-α, and LIF.

41. A medium according to claim 4, wherein said cytokines encompass three or more of thrombopoietin, flt-3 ligand, stem cell factor, G-CSF, GM-CSF, IL-6, MIP-I-α, and LIF.

42. A medium according to claim 17, wherein said cytokines encompass three or more of thrombopoietin, flt-3 ligand, stem cell factor, G-CSF, GM-CSF, IL-6, MIP-I-α, and LIF.

43. A medium according to claim 18, wherein said cytokines encompass three or more of thrombopoietin, flt-3 ligand, stem cell factor, G-CSF, GM-CSF, IL-6, MIP-I-α, and LIF.

44. A medium according to claim 19, wherein said cytokines encompass three or more of thrombopoietin, flt-3 ligand, stem cell factor, G-CSF, GM-CSF, IL-6,MIP-I-α, and LIF.

45. A medium according to claim 20, wherein said cytokines encompass three or more of thrornbopoietin, flt-3 ligand, stem cell factor, G-CSF, GM-CSF, IL-6, MIP-I-α, and LIF.

46. A medium according to claim 28, wherein said cytokines encompass three or more of thrombopoietin, flt-3 ligand, stem cell factor, G-CSF, GM-CSF, IL-6, MIP-I-α, and LIF.

47. A medium according to claim 29, wherein said cytokines encompass three or more of thrombopoictin, flt-3 ligand, stem cell factor, G-CSF, GM-CSF, IL-6 MIP-I-α, and LIF.

48. A medium according to claim 32, wherein said cytokines encompass three or more of thrombopoietin, flt-3 ligand, stem cell factor, G-CSF, GM-CSF, IL-6, MIP-I-α, and LIF.

49. A medium according to claim 33, wherein said cytokines encompass three or more of thrombopoietin, flt-3 ligand, stem cell factor, G-CSF, GM-CSF, IL-6, MIP-I-α, and LIF.

50. A medium according to claim 5, wherein said serum is AB.

51. A medium according to claim 24, wherein said serum is AB.

52. The medium of claim 2 wherein the medium comprises about 5 mmol/l of O-acetyl-L-carnitine in relation to the volume of culture medium.

53. The medium of claim 3 wherein the medium comprises about 60 mg/l of N-desulphated-N-acetylated heparin in relation to the volume of culture medium.

54. The stem cells of claim 22 wherein the stem cells are expanded.

55. The stem cells of claim 23 wherein the stem cells are expanded.

* * * * *